United States Patent
Samproni

(10) Patent No.: US 9,465,023 B2
(45) Date of Patent: Oct. 11, 2016

(54) DEVICE AND METHOD FOR UNIT USE SENSOR TESTING

(71) Applicant: Siemens Healthcare Diagnostics Inc., Tarrytown, NY (US)

(72) Inventor: Jennifer A. Samproni, Braintree, MA (US)

(73) Assignee: Siemens Healthcare Diagnostis Inc., Tarrytown, NY (US)

( * ) Notice: Subject to any disclaimer, the term of this patent is extended or adjusted under 35 U.S.C. 154(b) by 0 days.

(21) Appl. No.: 14/910,147

(22) PCT Filed: Jul. 31, 2014

(86) PCT No.: PCT/US2014/049181
§ 371 (c)(1),
(2) Date: Feb. 4, 2016

(87) PCT Pub. No.: WO2015/020880
PCT Pub. Date: Feb. 12, 2015

(65) Prior Publication Data
US 2016/0178606 A1 Jun. 23, 2016

Related U.S. Application Data

(60) Provisional application No. 61/862,245, filed on Aug. 5, 2013.

(51) Int. Cl.
G01N 33/487 (2006.01)
G01N 27/403 (2006.01)
G01N 33/52 (2006.01)
G01N 33/543 (2006.01)
B01L 3/00 (2006.01)

(52) U.S. Cl.
CPC ..... *G01N 33/4875* (2013.01); *B01L 3/502707* (2013.01); *B01L 3/502715* (2013.01); *G01N 27/403* (2013.01); *G01N 33/525* (2013.01); *G01N 33/54306* (2013.01); *B01L 2300/0627* (2013.01); *B01L 2300/0645* (2013.01); *B01L 2300/0861* (2013.01); *B01L 2300/0887* (2013.01)

(58) Field of Classification Search
CPC ............ G01N 27/403; G01N 33/487; G01N 33/525; G01N 33/543; B01L 3/502; B01L 2300/081; B01L 2300/064; B01L 2300/062; B01L 2300/088
See application file for complete search history.

(56) References Cited

U.S. PATENT DOCUMENTS

| | | | |
|---|---|---|---|
| 3,526,480 A | 9/1970 | Findl et al. | |
| 5,077,010 A | 12/1991 | Ishizaka et al. | |
| 5,208,163 A | 5/1993 | Charlton et al. | |
| 5,408,535 A | 4/1995 | Howard, III et al. | |
| 7,498,132 B2 | 3/2009 | Yu et al. | |
| 7,927,545 B2 | 4/2011 | Charlton | |
| 2011/0091357 A1 | 4/2011 | Blatt et al. | |

OTHER PUBLICATIONS

International Search Report and Written Opinion of International Application No. PCT/US2014/049181 dated Mar. 31, 2015.

*Primary Examiner* — Jennifer Dieterle
(74) *Attorney, Agent, or Firm* — Kyle D. Petaja

(57) ABSTRACT

An analyte testing material web, method of making the analyte testing material web, and an analyzer are disclosed. The analyte testing material web has a material web and a plurality of distinct sample testing devices. The material web has a first surface, a second surface opposite the first surface, a first side, and a second side. The plurality of sample testing devices are positioned on the first surface of the material web. Each of the plurality of sample testing devices has an inlet, an outlet, a fluid channel, and one or more testing elements within the fluid channel and configured to analyze one or more analyte within a sample applied to the inlet of one of the plurality of sample testing devices.

20 Claims, 7 Drawing Sheets

DEVICE AND METHOD FOR UNIT USE SENSOR TESTING

This application is the US National Stage of International Application No. PCT/US2014/049181, filed Jul. 31, 2014 and claims the benefit thereof. The International Application claims the benefit of U.S. Provisional Application No. 61/862,245, filed Aug. 5, 2013. All of the applications are incorporated by reference herein in their entirety.

BACKGROUND

A sensor, also called a detector, is a device that measures a physical quantity and converts it to a signal which may be read by an observer or by an instrument. For example, a mercury-in-glass thermometer converts the measured temperature into expansion and contraction of a liquid which may be read on a calibrated glass tube. A thermocouple converts temperature to an output voltage which may be read by a voltmeter. For accuracy, most sensors are calibrated against known standards.

Sensors may be used in chemical and biochemical testing to determine characteristics of an analyte of interest within a specimen or sample. In biomedicine and biotechnology, sensors which detect analytes having a biological component, such as cells, protein, or nucleic acid are called biosensors. Biosensors may be used for both in vitro and in vivo applications. In other fields of chemistry sensors may detect analytes having predetermined chemical compositions or chemical components. For example conductometric sensors may take conductivity measurements to measure hematocrit. In another example, ion selective electrodes may be used for biological and non-biological samples, such as testing for predetermined ions in water samples, for example. Sensors of these and other similar types may be used for industrial testing, agriculture, food testing, bioweapons testing, and drug use testing, for example.

Sensors may be exposed to a sample, such as blood, urine, interstitial fluid, body fluid specimens, organic chemical compounds, inorganic chemical compounds, and other samples having analytes of interest, and used to detect predetermined analytes within the sample. The sensor may then be exposed to a transducer or detector element which may work in a physiochemical manner using a sensing medium such as light, electricity, piezoelectric, electrochemical, or the like. In any event, the transducer or detector element transforms a signal from the sensor into another signal that may be more easily measured and quantified. The signal produced by the transducer or detector element may be provided to a reader device having associated electronics, signal processors, and/or a display to provide the results in a user readable format. For example, the results may be provided on a graphical display.

Test strips are widely used in the fields of clinical chemistry, biochemistry, and the medical field, among other industries. Test strips may have single or multiple sensors connected to the strip. Regardless of the amount of sensors, test strips are often single use tests which, once used, are discarded. Common examples of test strips are glucose strips and urine test strips. Some sensors, used in test strips, may undergo a color change in response to contact with a sample. For example, urine test strips often use color change sensors. Reagent test strips are widely used in the field of clinical chemistry and employ color changing sensors. A test strip usually has one or more test areas, also called reagent pads, and each test area is capable of undergoing a color change in response to contact with a liquid specimen, such as a biological or chemical sample. The liquid sample usually contains one or more analytes of interest. The presence and concentrations of these analytes of interest in the sample are determinable by an analysis of the color changes undergone by the reagent pads. Usually, this analysis involves a color comparison between the reagent pad and a color standard or scale. A reflectance spectroscope is commonly used to analyze analytes of interest applied to the reagent pads. A conventional spectrophotometer determines the color of a sample applied to one or more of the reagent pads disposed on a white, non-reactive surface by illuminating the pad and taking a number of reflectance readings from the pad, each having a magnitude relating to a different wavelength of visible light. Today, strip reading instruments employ a variety of area array detection readheads utilizing CCD (charge-coupled device), CID (charge-injection device) or PMOS detection structures for detecting color changes to the reagent pads. The color of the sample on the pad may then be determined based upon the relative magnitudes of red, green and blue reflectance signals.

Conventional spectrophotometers may be used, for example, to perform a number of different urinalysis tests utilizing a reagent strip on which a number of different reagent pads are disposed. Each reagent pad is provided with a different reagent which causes a color change in response to the presence of a certain type of constituent in a sample such as leukocytes (white blood cells), red blood cells, glucose, bilirubin, urobilinogen, nitrite, protein, ketone bodies, or other analytes of interest. The color developed in a particular analyte defines the characteristic discrete spectrum for absorption of light for that particular analyte. For example, the characteristic absorption spectrum for color-developed glucose falls within the upper end of the blue spectrum and the lower end of the green spectrum. Reagent strips may have ten different types of reagent pads.

Other optical readers are known that do not use reflectance, but rather capture an image of the test strips and convert the captured signal to RGB or to another format from which the color of the reagent pads on the test strip can be determined. See for example, U.S. Pat. No. 5,408,535, which is also assigned to the assignee of the present disclosure and is incorporated herein by reference in its entirety. These optical readers can also be used to read slides or other diagnostic tests.

Optical readers may be incorporated into automated instruments which read test strips or continuous testing material. The CLINITEK ATLAS automated urinalysis system, which is manufactured and sold by Siemens Healthcare Diagnostics, uses a cassette containing reagent areas mounted seriatim on a continuous plastic substrate which is wound into a reel rotatably housed in the cassette. Another continuous testing material is disclosed in U.S. Pat. No. 7,927,545.

Other sensors include conductometric sensors, electrochemical sensors, and amperometric sensors. Conductometric sensors or chemiresistors may operate on an impedance principle and be used to detect compounds such as hematocrit, for example. Conductometric sensors may operate by applying a material capable of changing its conductivity upon interaction with the analyte of interest. The material is placed between and in contact with two contact electrodes and the resistance of the electrodes and the material is measured. Conductometric sensors may also have the material layered atop an electrode and be provided with a counter-electrode to complete a circuit. Electrochemical sensors may be implemented as ion selective electrodes or potentiometric sensors which may measure values for pH, $Na^+$, $Ca^+$, $K^+$, $Cl^-$, or other ions, for example. Potentiometric sensors may operate by measuring a signal as a potential difference between a working electrode and a reference electrode where the potential of the working electrode is based on a concentration of the analyte of interest and the reference electrode provides a defined reference potential. Amperometric sensors may analyze samples for compounds such as enzymatic lactate, glucose, and creatinine, for example. Amperometric sensors may operate by passing a voltage potential between two electrodes positioned within a sample and measuring the current changes as an analyte of interest is oxidized at an anode electrode or reduced at a cathode electrode. The potential applied to the electrodes may be adjusted to tailor a response to a predetermined analyte of interest.

An interdigitated sensor array may be provided with at least two microelectrodes, both of which have fingers which are spaced apart and interleaved in an interdigitated fashion. Each of the microelectrodes is provided with a relatively large trace connected to a plurality of relatively fine traces. In biomedicine and biotechnology, the amount of analytes of interest within a sample is very small and difficult to detect. As such, amplification of the signal provides more accurate reading for a detected analyte.

Typically test strips or cartridges of the types described above are single use tests. These tests present issues of inventory management, where a user must store and track inventory in a centralized area to serve multiple single use test instruments. Included in the issue of inventory management, real time inventory may be of increased importance to determine when inventory of single use tests are low. Of note, is that there is no guarantee that all sensors within a lot of test strips have been stored in comparative conditions potentially leading to erroneous readings on test strips due to certain test strips within a lot being stored in differing ambient conditions. If a single use test strip fails, a sample may be lost and a user may be required to locate another test strip stored in appropriate conditions to retest a new sample. There exists a need for a multi-single use testing material and testing instrument which may streamline concerns of inventory, batch storage with regards to controlled or known conditions, instrument based inventory management, and similarity in treatment of sensors within a lot.

SUMMARY

The summary is provided to introduce a selection of concepts that are further described in the detailed description. This summary is not intended to identify key or essential features of the claimed subject matter, nor is it intended to be used as an aid in limiting the scope of the claimed subject matter.

In one embodiment, an analyte testing material web is described. The analyte testing material web has a material web and a plurality of distinct sample testing devices connected to the material web. The material web has a first surface, a second surface opposite the first surface, a first side, and a second side. The plurality of sample testing devices are positioned on the first surface of the material web. Each of the plurality of sample testing devices has an inlet, an outlet, a fluid channel, and one or more testing elements within the fluid channel and configured to analyze one or more analyte within a sample applied to the inlet of one of the plurality of sample testing devices. The testing elements may be implemented in a variety of manners, such as including a conductometric sensor, an amperometric sensor, an electrochemical sensor, a potentiometric sensor, as well as utilizing various types of reagents.

In one embodiment, the material web of the analyte testing material is a first material web. The plurality of sample testing devices are formed from the one or more testing elements connected to the first surface of the first material web, a second material web connected to the first material web, and a third material web connected to the second material web. The second material web has a first surface, a second surface opposite the first surface, a thickness extending between the first and second surfaces, and a plurality of openings. The second surface of the second material web is connected to the first surface of the first material web such that the plurality of openings form a plurality of wells defined by the thickness of the second material web and the first surface of the first material web. Each of the plurality of wells define the fluid channel of one of the sample testing devices encompassing at least one of the one or more testing elements. The third material web has a first surface, a second surface opposite the first surface, a thickness extending between the first and second surfaces, a plurality of inlets, and a plurality of outlets. The second surface of the third material web is connected to the first surface of the second material web such that certain of the plurality of inlets and certain of the plurality of outlets enable fluid communication with each of the plurality of wells. In one embodiment, each of the plurality of inlets of the third material web form the inlet of one of the sample testing devices and each of the plurality of outlets of the third material web form the outlet of one of the sample testing devices.

In another version, a method of making an analyte testing material web is described. The method is performed by applying a plurality of testing elements to a first surface of a first material web. The first material web has a first surface, a second surface opposite the first surface, and a thickness extending between the first and second surfaces. The method is further performed by applying a second material web to the first surface of the first material web. The second material web has a first surface, a second surface opposite the first surface, a thickness extending between the first and second surfaces, and a plurality of openings. The plurality of openings form a plurality of wells defined by the thickness of the second material web and the first surface of the first material web. Each of the plurality of wells defines a fluid channel encompassing at least one of the plurality of testing elements. The method is finally performed by applying a third material web to the first surface of the second material web. The third material web has a first surface, a second surface opposite the first surface, a thickness extending between the first and second surfaces, a plurality of inlets, and a plurality of outlets. The third material web is applied to the second material web such that certain of the plurality of inlets and certain of the plurality of outlets enable fluid communication with each of the plurality of wells.

In another embodiment, an analyzer is presented. The analyzer has a housing, a support member connected to an interior of the housing and having a plurality of advancement members, a motive source coupled to at least one of the plurality of advancement members, one or more reader, and a controller configured to cause the motive source to move the advancement member. The housing has one or more openings configured to receive an analyte testing material web and one or more sample for testing. The analyte testing material web has a plurality of distinct sample testing devices. The plurality of advancement members are configured to advance the plurality of distinct sample testing devices of the analyte testing material web to a read position. The motive source is configured to cause the plurality of advancement members to move the sample testing devices of the analyte testing material web to the read position. The one or more reader is configured to read the sample testing devices of the analyte testing material web in the read position, and produce and transmit testing signals. The controller is configured to cause the advancement members to move and thereby the sample testing devices of the analyte testing material web to the read position. The controller is also configured to receive testing signals indicative of testing the one or more sample using the analyte testing material web.

In yet another version, an analyte testing device is described. The analyte testing devices has a housing having at least one opening, a reel positioned within and supported by the housing, and an analyte testing material web connected to the reel and wound about the reel. The analyte testing material web has a material web and a plurality of distinct sample testing devices positioned on the material web. The material web has a first surface, a second surface opposite the first surface, a first side, and a second side opposite the first side. Each of the plurality of sample testing devices has an inlet, an outlet, a fluid channel, and one or more testing elements configured to analyze one or more sample applied to one or more of the plurality of distinct sample testing devices.

Additional features and advantages of the present disclosure will be made apparent from the following detailed description of illustrative embodiments that proceeds with reference to the accompanying drawings.

BRIEF DESCRIPTION OF THE DRAWINGS

A more complete appreciation of the present disclosure and many of the attendant advantages thereof will be readily understood by reference to the following detailed description when taken in conjunction with the accompanying drawings, in which.

DESCRIPTION OF THE PREFERRED EMBODIMENTS

The following detailed description refers to the accompanying drawings. The same reference numbers in different drawings may identify the same or similar elements.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements, but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more and the singular also includes the plural unless it is obvious that it is meant otherwise.

Further, use of the term "plurality" is meant to convey "more than one" unless expressly stated to the contrary.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Circuitry, as used herein, may be analog and/or digital, components, or one or more suitably programmed microprocessors and associated hardware and software, or hardwired logic. Also, "components" may perform one or more functions. The term "component," may include hardware, such as a processor, an application specific integrated circuit (ASIC), or a field programmable gate array (FPGA), or a combination of hardware and software. Software includes one or more computer executable instructions that when executed by one or more component cause the component to perform a specified function. It should be understood that the algorithms described herein are stored on one or more non-transient memory. Exemplary non-transient memory includes random access memory, read only memory, flash memory or the like. Such non-transient memory may be electrically based or optically based.

Throughout this document, the terms "couple" and "coupled" refer to elements which can be directly connected together or one or more intervening elements may also be present. In contrast, the terms "directly couple" and "directly coupled" refer to elements that are directly connected with no intervening elements present.

Figure 1:
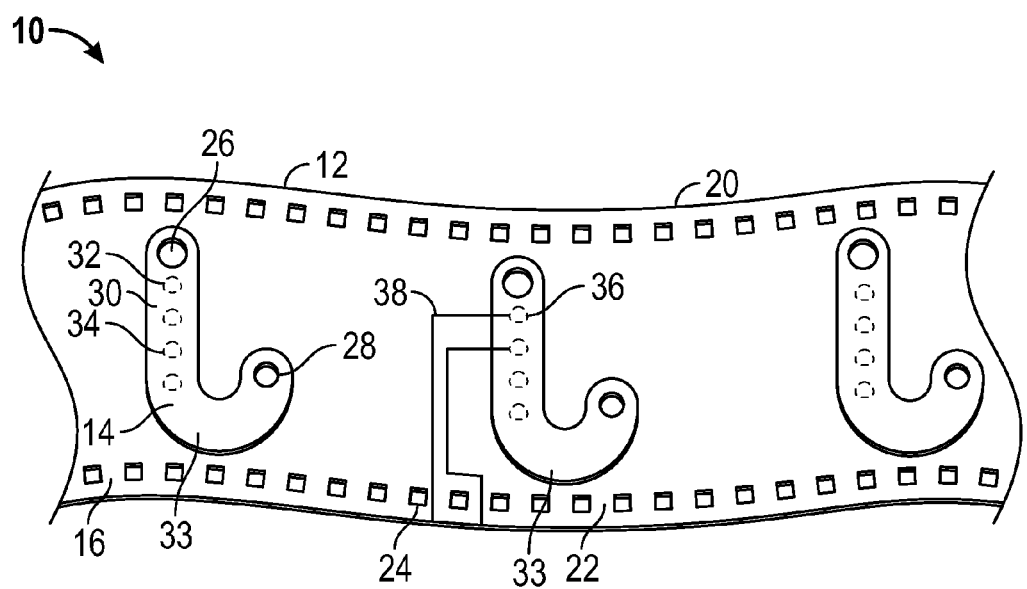
FIG. 1 shows a perspective view of an analyte testing material web in accordance with the present disclosure.
Figure 2:
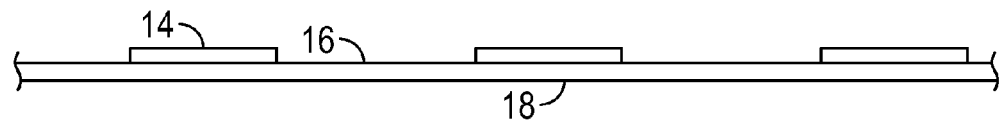
FIG. 2 shows a side view of the analyte testing material web of FIG. 1.

Referring now to the figures and in particular to FIGS. 1 and 2, shown therein is one embodiment of an analyte testing material web 10 having a material web 12 and a plurality of distinct sample testing devices 14 positioned on the material web 12. The material web 12 is provided with a first surface 16, a second surface 18 opposite the first surface 16, a first side 20, and a second side 22 opposite the first side 20. The material web 12 may be formed from flexible materials such as foils, metallic foils, flexible polymers, polyethylene terephthalate (PET), polyimide (PI), adhesives, and other suitable flexible materials such as those used in the flexible printed electronics industry. The material web 12 may be less than one inch in width from the first side 20 to the second side 22 to two feet in width. In one embodiment, the material web 12 may have multiple rows of distinct sample testing devices 14 extending across the width. In another embodiment, the material web 12 may have a single row of distinct sample testing devices 14 positioned in a generally central location within the width of the material web 12. The material web 12 may be a continuous material web of any suitable length desired and may be flexible such that the material web 12 may be wound around a device. In one embodiment, the material web 12 may be provided with perforations 24 substantially adjacent to the first and second sides 20 and 22. The perforations 24 may be configured to enable advancement of the material web 12 via one or more sprocket-wheels.

The plurality of distinct sample testing devices 14 are positioned on the first surface 16 of the material web 12. Each of the plurality of distinct sample testing devices 14 has an inlet 26 configured to receive a sample, an outlet 28 configured to allow the passage of air or sample from within the sample testing device 14, a fluid channel 30 configured to direct the sample, received from the inlet 26, through the sample testing device 14, and one or more testing elements 32 within the fluid channel 30 and configured to analyze one or more analyte within the sample applied to one or more of the plurality of distinct sample testing devices 14. The sample testing devices 14 may be positioned on the material web 12 spaced a distance apart from one another along the material web 12. The sample may be a biological specimen, such as blood, semen, interstitial fluid, urine, or other biological specimen, for example. The sample may also be non-biological in nature, such as inorganic chemical compounds, organic chemical compounds, and other fluid samples containing analytes of interest, for example. The sample may be directed through the fluid channel 30 via capillary action, by one or more pumps connected to either the inlet 26 or the outlet 28, or by one or more valves connected to the inlet 26, the outlet 28, or positioned within the fluid channel 30. The sample may be introduced to the sample testing device 14 through the inlet 26 by pipette, pump, valve, or other suitable device, and may be introduced manually by a user, automatically via an analyzer, described below, or semi-automatically via the analyzer where prompted by a user.

The sample testing devices 14 may be linearly shaped, shaped in a "J" formation, or be formed in any other suitable shape, such that the sample testing devices 14 are provided with an overflow area 33. The overflow area 33 may allow a sample to pass over the one or more testing elements 32 by capillary action, by one or more pump, or by one or more valve. Once the sample contacts the sample testing device 14, portions of the sample may be contaminated, by picking up $O_2$ from the plastic or contaminants from an adhesive, for example. The overflow area 33 may receive the contaminated portion of the sample so that an uncontaminated portion of the sample remains in contact with the one or more testing elements 32. In one embodiment, the overflow area 33 may be provided with a wicking pad to receive and absorb the contaminated portion of the sample. In some embodiments, the sample testing devices 14 may be microfluidic devices, mesofluidic devices, or other similar devices applied to the material web 12.

The outlet 28 may allow the passage of air or a portion of the sample received through the inlet 26 to escape the sample testing device 14. In one embodiment, the outlet 28 may be provided with a porous material extending across the outlet and configured to act as an air vent, releasing air from the sample testing device 14, and configured to well and seal the pores when exposed to the sample to create a barrier upon exposure to the liquid sample, thereby preventing escape of the sample from the sample testing device 14. In another embodiment, the outlet 28 may be configured to allow a portion of the sample to pass through the sample testing device 14 and be transferred to a waste repository (not shown). In yet another embodiment, the outlet 28 may be formed from a wicking material capable of allowing air passage through the sample testing device 14 and configured to receive and absorb at least a portion of the sample received through the inlet 26 of the sample testing device 14.

In embodiments where a plurality of testing elements 32 are positioned within the fluid channel 30, the testing elements 32 may be positioned within the fluid channel 30 and spaced a distance apart from one another along the fluid channel 30. In another embodiment employing a plurality of testing elements 32, certain of the plurality of testing elements 32 may be positioned in the fluid channel 30 and grouped together to form one or more testing groups 34. Where there are a plurality of testing groups 34, the testing groups 34 may be positioned within the fluid channel 30 and spaced a distance apart from one another within the fluid channel 30.

In one embodiment, the one or more testing elements 32 may be implemented in a variety of manners, such as including a conductometric sensor, an amperometric sensor, an electrochemical sensor, a potentiometric sensor, as well as utilizing various types of reagents. For example, the one or more testing elements 32 may be in the form of electrochemical sensors having at least one electrode 36 and at least one contact 38. The electrode 36 may be configured for sample measurement and separated a distance from another of the one or more testing elements 32. The electrode 36 and the contact 38 may be positioned within the fluid channel 30 by screen printing, stencil, ink jetting, aerosol jetting, electrodeposition, rotogravure, or any other suitable method. The contact 38 contacts the electrode 36 and may be configured to electrically connect the electrode 36 to a reader (not shown) of an analyzer (not shown) to transmit signals generated by the electrode 36 to the reader for testing the one or more analyte within a sample. In one embodiment, the contact 38 and the electrode 36 may be positioned on the first surface 16 of the material web 12. In another embodiment, the electrode 36 may be positioned on the first surface 16 of the material web 12 and the contact 38 may be positioned on the second surface 18 of the material web 12 with the contact 38 connected to the electrode 36 by vias extending through a thickness of the material web 12 between the first and second surfaces 16 and 18.

Where a sample testing device 14 is provided with a plurality of testing elements 32 in the form of electrodes 36 creating electrochemical sensors, the electrodes 36 may be defined as working electrodes, reference electrodes, and sample recognition electrodes. A sample measurement signal may be applied when the working electrode and the reference electrode are in use for measurement of analytes within the sample. The spaced apart positioning of the electrodes 36 enable response signals between the working and reference electrodes to be effectively detected.

In one embodiment, the one or more testing elements 32 may be formed from one or more dry reagent material or one or more liquid reagent material. The one or more dry reagent may be reagents used in immunochemistry testing; reagent pads; reagent papers; dry reagents used for glucose testing blood, urine, adulterants for urine samples; dendrimers based reagents; and other dry reagents suitable for testing for predetermined analytes of interest within a sample. The reagents used in these embodiments may contain indicator dyes, metals, enzymes, polymers, antibodies, electrochemically reactive ingredients and various other chemicals dried onto carriers or suspended in liquid. The one or more liquid reagent material may be similar to the dry reagent materials but suspended in a liquid solution. In one embodiment, the one or more testing elements 32 may be formed from reagent pads where a reagent pad may be impregnated with the reagents used in either the dry reagent embodiments or the liquid reagent embodiments.

Referring now to FIGS. 3-6, therein shown is another embodiment of the analyte testing material web 10. The analyte testing material web 10 may be formed from a plurality of material webs, where the material web 12 serves as a base substrate and the plurality of sample testing devices 14 are formed from a plurality of material webs and the one or more testing devices combined together. For example, as shown, the analyte testing material web 10 may be formed from a first material web 50, which may be the same or similar to the material web 12. The plurality of sample testing devices 14 may be formed from the one or more testing elements 32, a second material web 52, and a third material web 54, where the one or more testing elements 32, the second material web 52, and the third material web 54 are applied to the first material web 50. The first material web 50 may be provided with a first surface 56, a second surface 58 opposite the first surface 56, a first side 60, and a second side 62 opposite the first side 60, similar to the material web 12. The first, second, and third material webs 50, 52, and 54 may be formed from differing material webs, such as metal foils, non-metal foils, flexible polymers, PET, PI adhesives, and other suitable materials, as previously described in relation to the material web 12.

Figure 3:
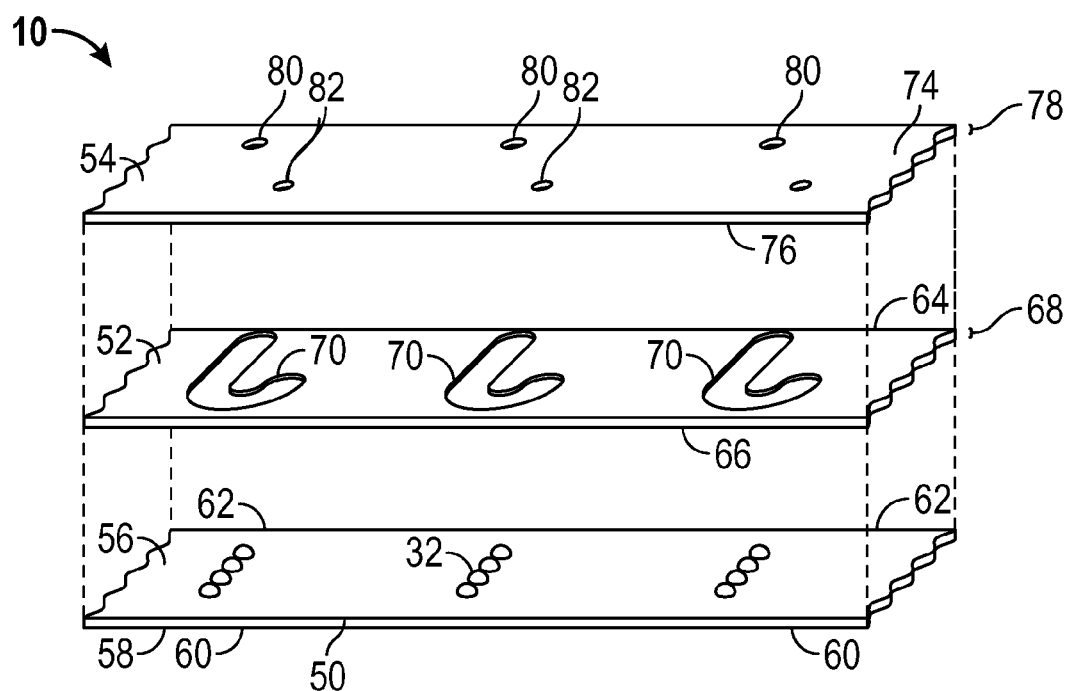
FIG. 3 is an exploded view of one embodiment of an analyte testing material web formed from a first, second, and third material web in accordance with the present disclosure.
Figure 4:
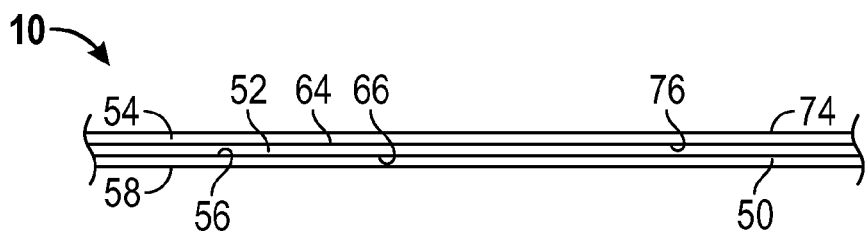
FIG. 4 shows a side view of the analyte testing material web of FIG. 3.
Figure 5:
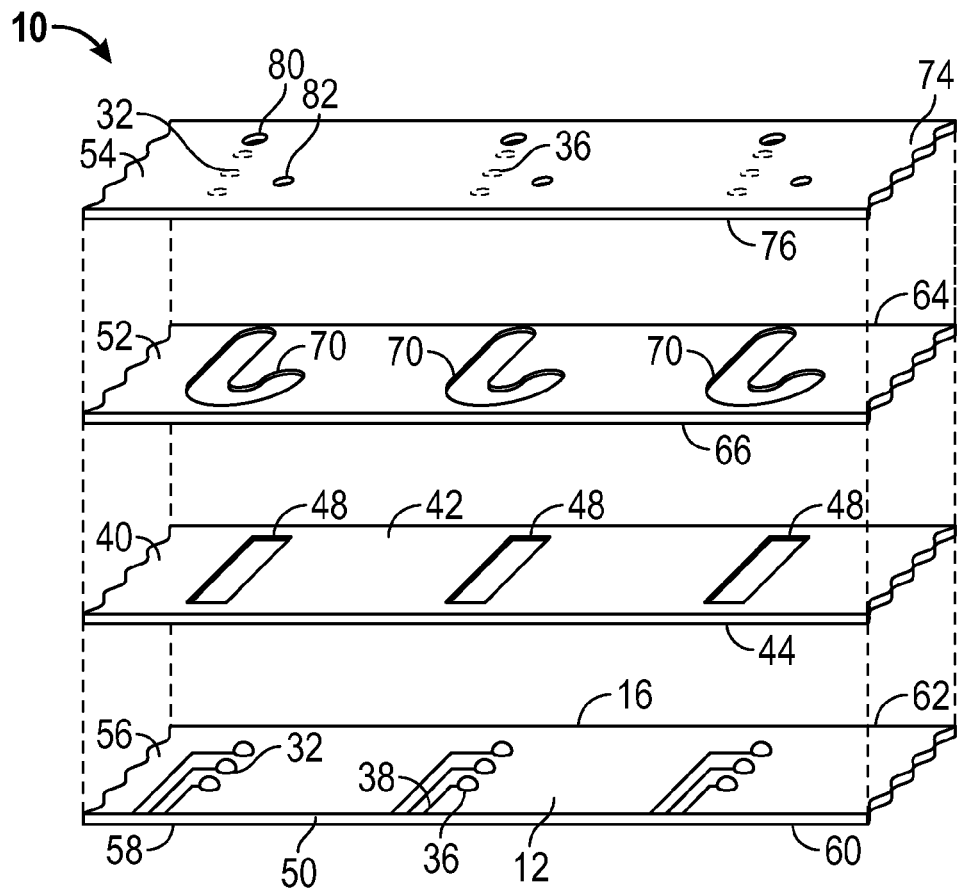
FIG. 5 is an exploded view of another embodiment of an analyte testing material web formed from a first, second, and third material web and a dielectric material web in accordance with the present disclosure.
Figure 6:
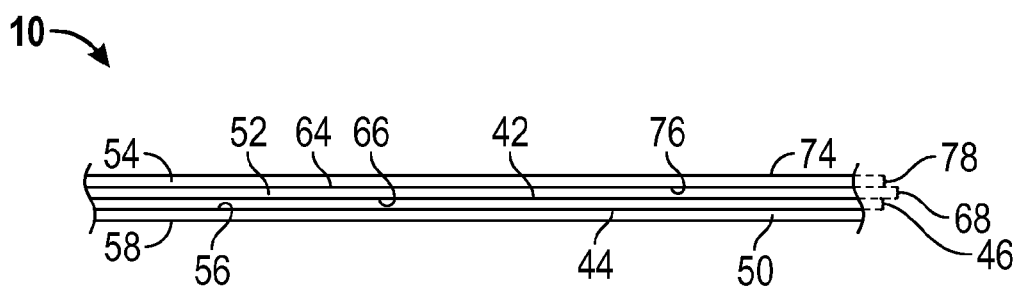
FIG. 6 shows a side view of the analyte testing material web of FIG. 5.

The one or more testing elements 32 may be applied to the first surface 56 of the first material web 50. The one or more testing elements 32 may be implemented as electrochemical sensors having electrodes and contacts, dry reagent material, or reagent pads, as described in detail above. As shown in FIG. 3, and described above, the one or more testing elements 32 may be dry reagent material, reagent pads, or other suitable materials. As shown in FIG. 5, and described above, the one or more testing elements 32 may be one or more electrochemical sensors, each having at least one electrode 36 and at least one contact 38.

The second material web 52 may be provided with a first surface 64, a second surface 66 opposite the first surface 64, a thickness 68 extending between the first and second surfaces 64 and 66, and a plurality of openings 70. The second material web 52 may be connected or applied to the first material web 50 such that the second surface 66 of the second material web 52 is connected to the first surface 56 of the first material web 50. The second material web 52 may be connected and positioned on the first material web 50 such that the plurality of openings 70 form a plurality of wells 72. The plurality of wells 72 are defined by the thickness 68 of the second material web 52 and the first surface 56 of the first material web 50. Each of the plurality of wells 72 may define the fluid channel 30 of one of the sample testing devices 14 encompassing at least one of the one or more testing elements 32. The second material web 52 may be connected to the first material web 50 via adhesives, cohesives, heating, or other suitable methods. In one embodiment, the second material web 52 may be a pressure sensitive adhesive layer between the first material web 50 and the third material web 54. In one embodiment, the second material web 52 may be a laminate formed of PET, PI, flexible polymers, and other suitable materials as described above in reference to the material web 12. In one embodiment, the one or more testing elements 32 may be applied to the first material web 50 through the plurality of wells 72 after the second material web 52 has been connected to the first material web 50.

The third material web 54 may be provided with a first surface 74, a second surface 76 opposite the first surface 74, a thickness 78 extending between the first and second surfaces 74 and 76, a plurality of inlets 80, and a plurality of outlets 82. The third material web 54 may be applied or connected to the second material web 52 such that the second surface 76 of the third material web 52 connects to the first surface 64 of the second material web 52. The third material web 54 may be connected and positioned on the second material web 52 such that certain of the plurality of inlets 80 and certain of the plurality of outlets 82 enable fluid communication with each of the plurality of wells 72. In this embodiment, each of the plurality of inlets 80 form the inlet 26 of one of the sample testing devices 14 and each of the plurality of outlets 82 form the outlet 28 of one of the sample testing devices 14. The third material web 54 may be connected to the second material web 52 via adhesive, heating, laser welding, thermal tacking, ultrasonic bonding, adhesive, cohesive, or any other suitable method. The third material web 54 may be formed from metal foils, non-metal foils, flexible polymers, PET, PI, and other suitable materials, as previously described in relation to the material web 12. The plurality of inlets 80 may be circular, triangular, square, or any other suitable shape. The plurality of outlets 82 may be any suitable shape. In one embodiment, the outlets 82 may be an overflow chamber in fluid communication with the fluid channel 30 and defined by the opening 48 of the second material web 52. In this embodiment, the outlet 82 may function to receive overflow from the fluid channel 30 without the possibility of releasing a portion of the sample. In another embodiment, the outlets 82 may include a material which, when in contact with the sample introduced through the inlet 80 and passing through the fluid channel 30 may seal the outlet to trap the sample and prevent excess sample from leaking from the sample testing device 14. The material may be formed from a wicking material, a polyacrylamide gel, a waste pad, paper with a desiccant or drying agent, a multi-posted liquid reagent or sample sink, or other suitable material to trap and retain excess sample.

In the embodiment, as shown in FIG. 5 where the electrodes 36 and the contacts 38 are positioned on the first surface 16 of the material web 12, a dielectric material web 40 may be positioned to cover and thereby isolate the contacts 38. The dielectric material web 40 may have a first surface 42, a second surface 44 opposite the first surface 42, a thickness 46 extending between the first and second surfaces 42 and 44, and a plurality of openings 48. The dielectric material web 40 may be positioned on the material web 12 such that the plurality of openings 48 of the dielectric material web 40 align with the inlet 26 and the outlet 28 of a sample testing device 14 to allow the sample to be introduced to the sample testing device 14 while isolating the contacts 38.

FIG. 5 also shows an embodiment in which the one or more testing elements 32 are positioned on the second surface 76 of the third material web 54 and the first surface 56 of the first material web 50. In this embodiment, the sample introduced through the inlet 80 simultaneously contacts certain of the one or more testing elements 32 of the first and third material webs 50 and 54 as the sample travels along the fluid channel 30. In this embodiment, the one or more testing elements 32 may be positioned on the third material web 54 in the same or similar manner as the one or more testing elements 32 described above. Additionally, the one or more testing elements 32 may be implemented similarly or the same as described above. In one embodiment, the one or more testing elements 32 on the third material web 54 and those on the first material web 50 may be of the same type, for example, where the one or more testing elements 32 are electrodes and certain of the one or more testing elements 32 of the third material web 54 and certain of the one or more testing elements 32 of the first material web 50 complete a circuit and enable analysis of the analyte of interest within the sample. In another embodiment, the one or more testing element 32 of the third material web 54 and those of the first material web 50 may be of differing types, for example, where the one or more testing elements 32 of the third material web comprise dry reagents, reagent pads, or the like and the one or more testing elements 32 of the first material web 50 comprise electrodes. In a further embodiment, certain of the one or more testing elements 32 of the first and third material webs 50 and 54 may be of a first type and certain of the one or more testing elements 32 of the first and third material webs 50 and 54 may be of a second type.

Shown in FIGS. 3-6 is also an exemplary embodiment of a method for making the analyte testing material web 10. The method may be performed by applying the plurality of testing elements 32 to the first material web 50, as previously described above. The second material web 52 may be applied to the first material web 50 such that the second surface 66 of the second material web 52 is connected to the first surface 56 of the first material web 50. The second material web 52 may be applied to the first material web 50 such that the plurality of openings 70 form the plurality of wells 72 defining the fluid channels 30 of the plurality of sample testing devices 14. The third material web 54 may be applied to the second material web 52 such that the second surface 76 of the third material web 54 is connected to the first surface 64 of the second material web 52. The third material web 54 may be applied to the second material web 52 such that certain of the plurality of inlets 80 and certain of the plurality of outlets 82 enable fluid communication with each of the plurality of wells 72. The first, second, and third material webs 50, 52, and 54 may be applied to one another as previously described above, for example using an adhesive. The method may further be performed by applying the dielectric material web 40 between the first surface 56 of the first material web 50 and the second surface 66 of the second material web 52. The dielectric material web 40 may be connected and positioned such that the openings 48 of the dielectric material web 40 align with the plurality of openings 70 of the second material web 52. The method may be further performed by perforating at least one of the first, second, and third material webs 50, 52, and 54. The perforations 24 enable the advancement of the first, second, and third material webs 50, 52, and 54.

Figure 7:
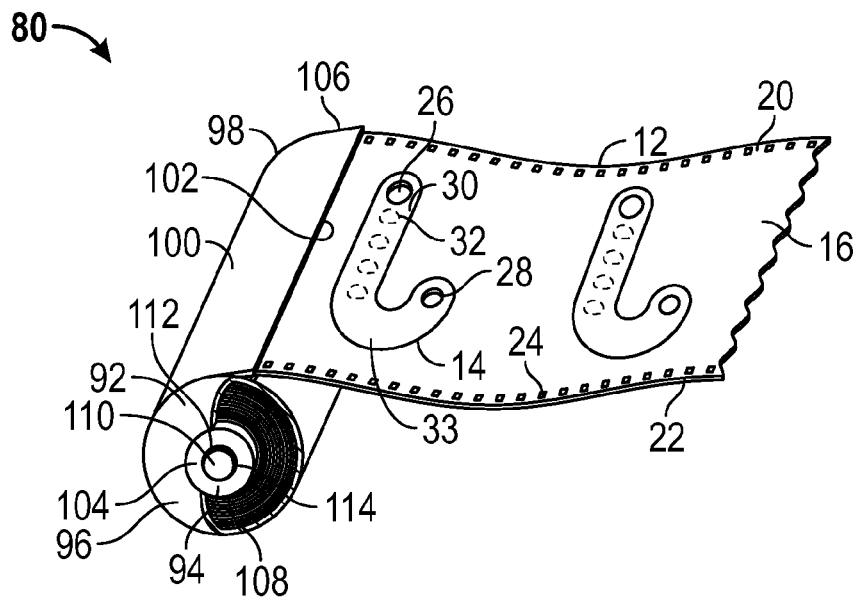
FIG. 7 shows an embodiment of a multi-single use analyte testing cassette in accordance with the present disclosure.

Referring now to FIG. 7, therein shown is one embodiment of a multi-single use analyte testing device 90 capable of holding a plurality of single use sample testing devices 14 spaced apart on the material web 12 to enable fewer instances of mishandling and contamination of samples being tested and limit contact with previously tested samples. The analyte testing device 90 comprises a housing 92, a reel 94 positioned within and supported by the housing 92, and the analyte testing material web 10 connected to and wound about the reel 94. The housing 92 may be provided with a first end 96, a second end 98 opposite the first end 96, a sidewall 100 extending between the first and second ends 96 and 98, and an opening 102 within the sidewall 100. The housing 92 may be configured to encompass the reel 94 and the analyte testing material web 10 wound about the reel 94. The opening 102 may be sized and shaped to allow passage of a free end of the analyte testing material 10 through the opening 102. A portion of the analyte testing material web 10 passing through the opening 102 may allow a user to expose one or more of the plurality of sample testing devices 14 and thereby enable the user to introduce one or more sample to the inlet 26 of one or more of the sample testing devices 14 to test for analytes of interest within the one or more sample. The housing 92 may be formed from plastic, metal, or any other suitable material or combination of materials.

The reel 94 may extend between the first and second ends 96 and 98 of the housing 92 and rotate freely within the housing 92 to enable the analyte testing material web 10 to be fed through the opening 102 of the housing 92. The reel 94 may be provided with a first end 104, a second end 106 opposite the first end 104, an exterior sidewall 108 extending between the first and second ends 104 and 106, an opening 110 positioned within the first and second ends 104 and 106 defined by an interior sidewall 112, and a plurality of ridges 114 positioned along the interior sidewall 112. The opening 110 may be surrounded by the plurality of ridges 114 extending inwardly into the opening 110. The ridges 114 may provide one or more surface by which to advance the reel 94 thereby enabling the analyte testing material web 10 to be fed through the opening 102 of the housing 92.

The analyte testing material web 10 may be implemented as described above and may be connected to the reel 94 and wound about the reel 94. The analyte testing material 10 may be connected to the reel by adhesive, a gripping mechanism, a fitting, or any other suitable manner.

Figure 8:
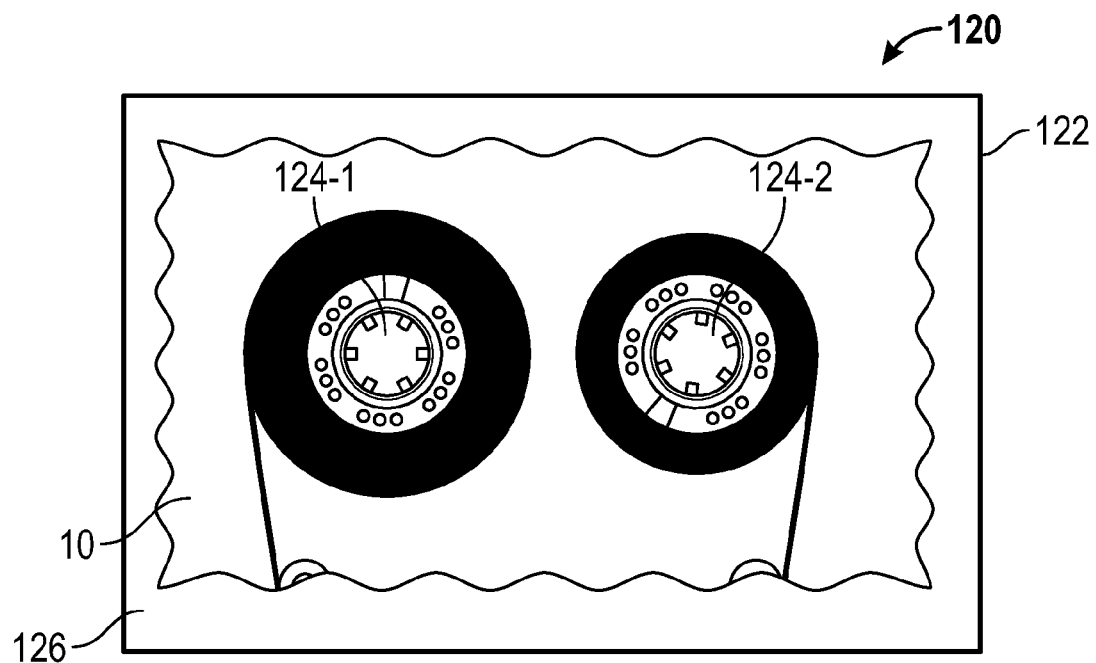
FIG. 8 is a partial elevational view of another embodiment of a multi-single use analyte testing cassette in accordance with the present disclosure.
Figure 9:
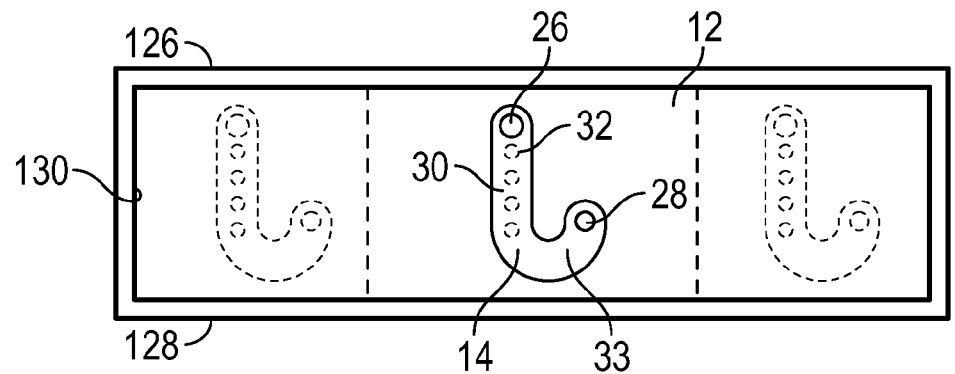
FIG. 9 shows a bottom plan view of the multi-single use analyte testing cassette of FIG. 8.

Referring now to FIG. 8 and 9, therein shown is another embodiment of an analyte testing device 120 which is provided with a housing 122, a first reel 124-1 and a second reel 124-2 positioned within and supported by the housing 122, and the analyte testing material web 10 connected to and at least partially wound around the first and second reels 124-1 and 124-2. The housing 122 may be provided with a first side 126, a second side 128 opposite the first side 126, and an opening 130 extending at least partially between the first and second sides 126 and 128. The opening 130 may be configured to expose a portion of the analyte testing material web 10 being advanced across the opening 130 to enable application of a sample to the inlet 26 of one or more of the plurality of sample testing devices 14 on the analyte testing material web 10. The housing 122 may be formed from plastic, metal, or any other suitable material or combination of materials. The first and second reel 124-1 and 124-2 may be implemented substantially similarly to the reel 94. The analyte testing material 10 may be implemented as described above.

Figure 10A:
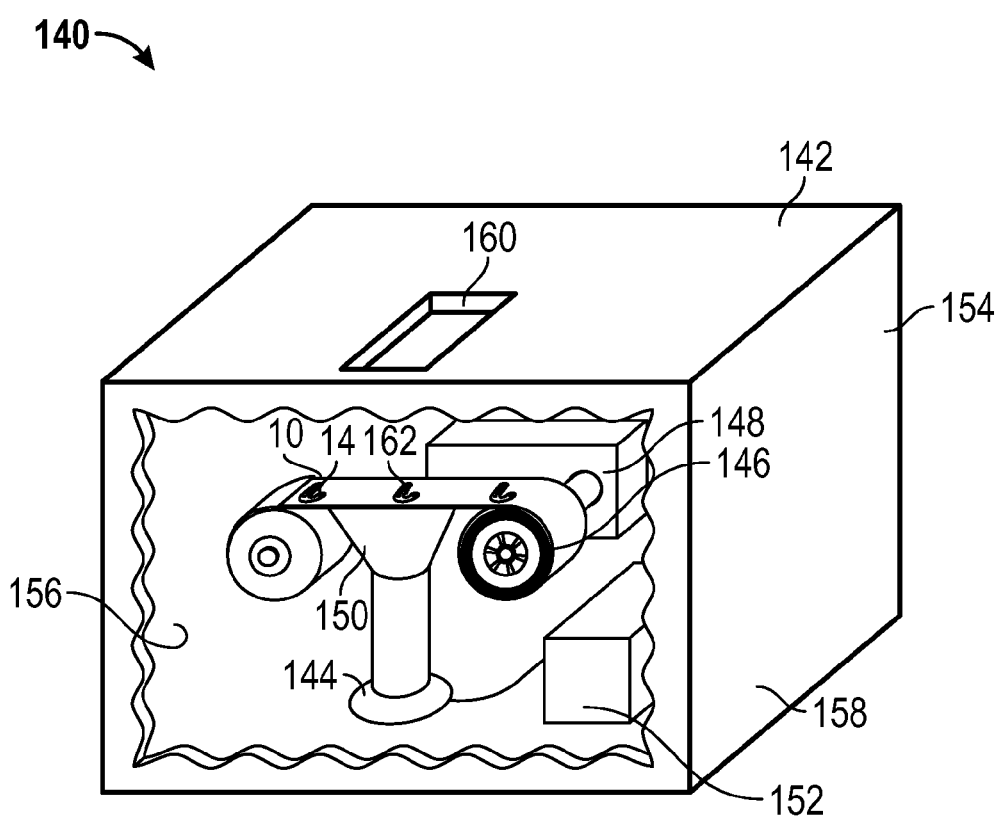
FIG. 10A shows a partial cross-sectional view of an analyzer in accordance with the present disclosure.
Figure 10B:
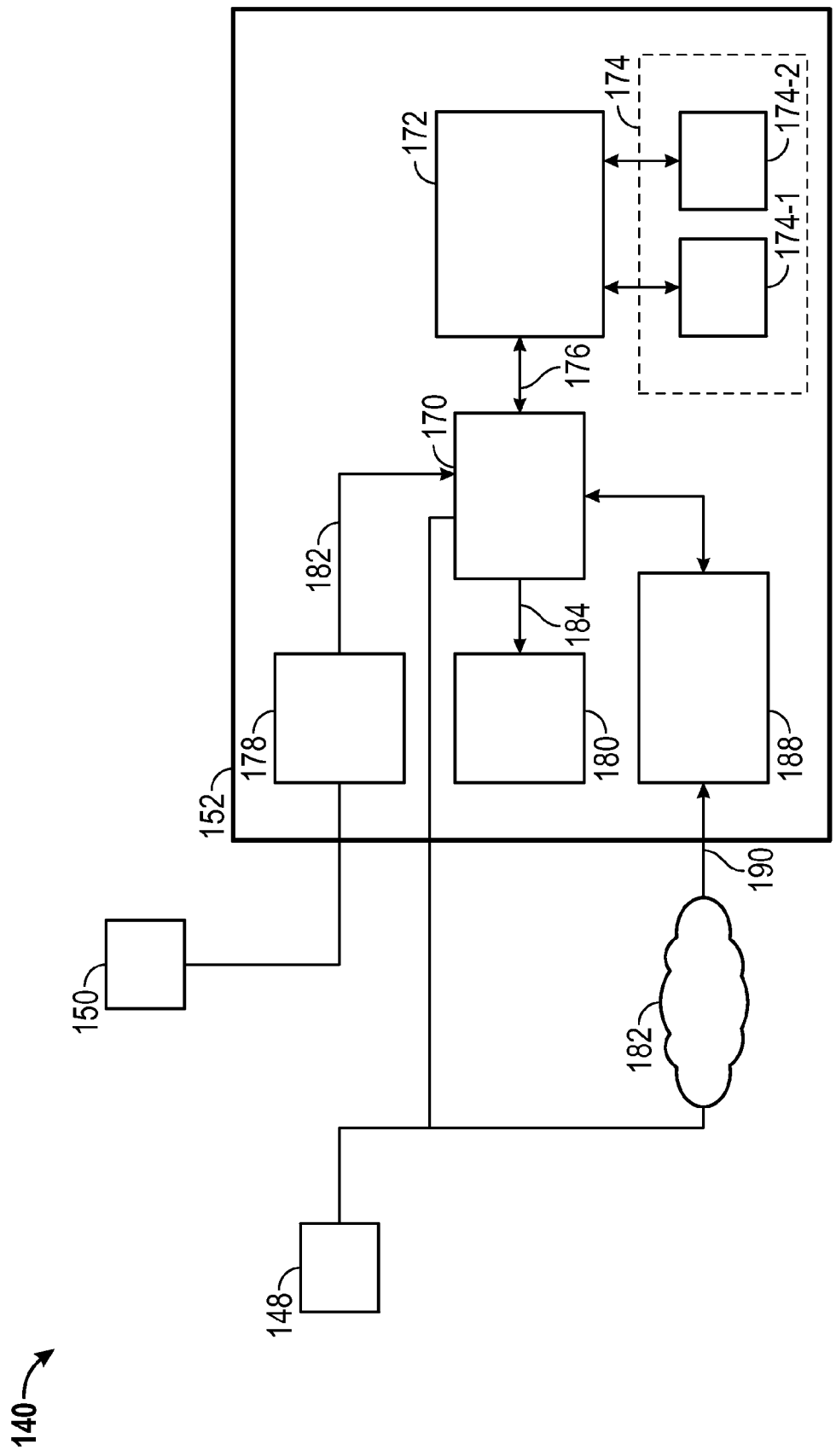
FIG. 10B shows a block diagram of various components of the analyzer of FIG. 10A including one embodiment of a controller in accordance with the present disclosure.

Referring now to FIGS. 10A and 10B, therein shown is a perspective view of an exemplary embodiment of an analyzer 140 according to the inventive concepts disclosed herein. The analyzer 140 may accept analyte testing devices, such as analyte testing device 90 or 120, having different predetermined types of sample testing devices 14, and testing elements 32. Each analyte testing device may have differing types of sample testing devices 14 and testing elements 32, for example differing electrodes, dry reagents, gels, reagent pads, blister pouches containing liquid reagents, or other suitable testing elements 32, and capable of testing for differing analytes within a sample to be tested. The analyzer 140, capable of receiving differing analyte testing devices, therefore may act as a multiuse analyzer for a wide variety of samples, for example, blood, glucose, saliva, enzymes, interstitial fluid, urine, non-biological chemical compounds, or other samples containing analytes of interest to be analyzed. The analyzer 140 may be provided with a housing 142, a support assembly 144 connected to the housing 142 having a plurality of advancement members 146, a motive source 148 coupled to at least one of the plurality of advancement members 146, one or more reader 150 configured to read the sample testing devices 14 of the analyte testing material web 10, and a controller 152 coupled to the motive source 148 configured to cause the motive source 148 to move the plurality of advancement members 146.

The housing 142 may be implemented as any suitable housing configured to receive the analyte testing material web 10, or the analyte testing device 90, or the analyte testing device 120 and the one or more sample, such that the analyte testing material web 10 may be inserted into the housing 142 and the one or more sample may be applied to the inlet 26 of one or more of the sample testing device 14 positioned on the analyte testing material web 10. For example, the housing 142 may have a plurality of sides 154, defining an interior 156 and an exterior 158, and one or more openings 160. Certain of the one or more openings 160 may be configured to receive the analyte testing material web 10 or the analyte testing device 90 and certain of the one or more openings 160 may be configured to receive the one or more sample for testing. The housing 142 may be formed from plastic, metal, or any other suitable material or combination of materials. The certain openings 160 configured to receive the one or more sample for testing may enable introduction of the sample to the analyte testing material web 10 via pipette, pump, valve, or other suitable device. For example, in one embodiment, the analyzer 140 may be positioned such that an automated pipette may pass through the opening 160 and introduce the sample for testing to the analyte testing material web 10. In another embodiment, the analyzer 140 may be configured with an introduction mechanism (not shown), such as one or more pipette, pump, or valve. The introduction mechanism may introduce the one or more sample for testing to the analyte material web 10 manually under the control of a user, automatically, controlled by the controller 152, or semi-automatically controlled by the controller 152 at the prompt of a user, for example.

The support assembly 144 may be connected to the interior 156 of the housing 142 and the plurality of advancement members 146. The support assembly 144 is configured to support the analyte testing material web 10 and enable the advancement of the distinct sample testing devices 14 of the analyte testing material web 10 to a read position 162. The read position 162 may be a position of the analyte testing material web 10 where one of the plurality of sample testing devices 14 is aligned for testing by the one or more reader 150. For example, where the one or more reader 150 is an optical sensor, the read position 162 may be a position such that the reader 150 may capture images of one of the sample testing devices 14 to be tested. As another example, the read position 162 may be a position where the trace, circuitry, or electrical contact of the one or more reader 150 electrically couples to the contacts 38, also known as a trace or electrical contact, of one of the sample testing devices 14, where the one or more reader 150 is a trace or circuitry capable of electrically coupling to the sample testing devices 14. In this embodiment, the one or more reader 150 may produce testing signals due to one or more interaction of the sample and the one or more testing elements 32. Additionally, the one or more reader 150 may apply a voltage or signal to the one or more testing elements 32 to produce or amplify the one or more interaction between the sample and the one or more testing elements 32. The plurality of advancement members 146 may be implemented as reels, sprocket-wheels, rollers, actuators, any other suitable mechanism, or combinations thereof. Certain of the plurality of advancement members 146 may be configured to engage reels 94, 124-1, and 124-2 of an analyte testing device 90 or 120, explained in further detail below, which may contain the analyte testing material web 10.

The motive source 148 may be coupled to at least one of the plurality of advancement members 146 and configured to cause the coupled advancement member 146 to move the sample testing devices 14 of the analyte testing material web 10 to and past the read position 162. The motive source 148 may be implemented as a motor, a linear actuator, a solenoid connected to a suitable linkage, or any other suitable mechanism configured to cause one or more of the plurality of advancement members 146 to advance the sample testing devices 14 on the analyte testing material web 10.

The one or more reader 150 is configured to produce testing signals indicative of the sample testing devices 14 testing the sample for the analyte of interest. The one or more reader 150 may then transmit the testing signals to the controller 152 for processing and display. In one embodiment, the one or more reader 150 may be implemented as a camera, CCD, 2D CCD, CMOS, or any other suitable image capture device or device configured to detect optical signals or light and to convert optical signals into electrical signals. The one or more reader 150 may be configured to detect an optical signal or light reflected from the one or more testing element 32, where the one or more testing element 32 presents an optically detectable indicator in response to testing the sample for the analyte of interest. In another embodiment, the one or more reader 150 may be implemented as circuitry and/or traces, for example, configured to electrically couple with the one or more testing element 32 when the sample testing device 14 is in the read position 162. In yet another embodiment, the one or more reader 150 may be implemented as a plurality of readers 150, the plurality of readers 150 being a combination of readers configured to detect optical or electrical signals caused by the readers coupling with the one or more testing element 32.

The controller 152 is configured to cause the advancement members 146 to move the sample testing devices 14 of the analyte testing material web 10 to the read position 162 and to receive the testing signals indicative of testing the one or more sample for the analyte of interest. In one embodiment, as shown in FIG. 10B, the controller 152 may comprise a processor 170, a non-transitory computer readable medium 172, and processor executable instructions 174 stored on the non-transitory computer readable medium 172. The controller 152 may further comprise a plurality of sensors coupled to the controller for determining characteristics of the sample in addition to the characteristics determined by the one or more reader 150. For example, the controller 152 may have a temperature sensor and a humidity sensor for determining the temperature and humidity of the sample.

The processor 170 may be implemented as a single processor or multiple processors working together or independently to execute the processor executable instructions 174 described herein. Embodiments of the processor 170 may include a digital signal processor (DSP), a central processing unit (CPU), a microprocessor, a multi-core processor, an application specific integrated circuit, and combinations thereof. The processor 170 is coupled to the non-transitory computer readable medium 172. The non-transitory computer readable medium 172 can be implemented as RAM, ROM, flash memory or the like, and may take the form of a magnetic device, optical device or the like. The non-transitory computer readable medium 172 can be a single non-transitory computer readable medium, or multiple non-transitory computer readable mediums functioning logically together or independently.

The processor 170 is coupled to and configured to communicate with the non-transitory computer readable medium 172 via a path 176 which can be implemented as a data bus, for example. The processor 170 may be capable of communicating with an input device 178 and an output device 180 via paths 182 and 184, respectively. Paths 182 and 184 may be implemented similarly to, or differently from path 176. For example, paths 182 and 184 may have a same or different number of wires and may or may not include a multidrop topology, a daisy chain topology, or one or more switched hubs. The paths 176, 182 and 184 can be a serial topology, a parallel topology, a proprietary topology, or combination thereof. The processor 170 is further capable of interfacing and/or communicating with one or more network 186, via a communications device 188 and a communications link 190 such as by exchanging electronic, digital and/or optical signals via the communications device 188 using a network protocol such as TCP/IP. The communications device 188 may be a wireless modem, digital subscriber line modem, cable modem, network bridge, Ethernet switch, direct wired connection or any other suitable communications device capable of communicating between the processor 170 and the network 186.

It is to be understood that in certain embodiments using more than one processor 170, the processors 170 may be located remotely from one another, located in the same location, or comprising a unitary multicore processor (not shown). The processor 170 is capable of reading and/or executing the processor executable instructions 174 and/or creating, manipulating, altering, and storing computer data structures into the non-transitory computer readable medium 172.

The non-transitory computer readable medium 172 stores processor executable instructions 174 and may be implemented as random access memory (RAM), a hard drive, a hard drive array, a solid state drive, a flash drive, a memory card, a CD-ROM, a DVD-ROM, a BLU-RAY, a floppy disk, an optical drive, and combinations thereof. When more than one non-transitory computer readable medium 172 is used, one of the non-transitory computer readable mediums 172 may be located in the same physical location as the processor 170, and another one of the non-transitory computer readable mediums 172 may be located in a location remote from the processor 170. The physical location of the non-transitory computer readable mediums 172 may be varied and the non-transitory computer readable medium 172 may be implemented as a "cloud memory," i.e. non-transitory computer readable medium 172 which is partially or completely based on or accessed using the network 186.

The input device 178 transmits data to the processor 170, and can be implemented as a keyboard, a mouse, a touch-screen, a camera, a cellular phone, a tablet, a smart phone, a PDA, a microphone, a network adapter, a camera, a scanner, the one or more reader 150, and combinations thereof. The input device 178 may be located in the same location as the processor 170, or may be remotely located and/or partially or completely network-based. The input device 178 may be positioned on or within the housing 92 or separate from the housing 92. The input device 178 communicates with the processor 170 via path 182.

The output device 180 transmits information from the processor 170 to a user, such that the information can be perceived by the user. For example, the output device 180 may be implemented as a server, a computer monitor, a cell phone, a tablet, a speaker, a website, a PDA, a fax, a printer, a projector, a laptop monitor, and combinations thereof. The output device 180 communicates with the processor 170 via the path 184. The output device 180 may be positioned on or within the housing 142 or separate from the housing 142.

The network 186 may permit bi-directional communication of information and/or data between the processor 170, the network 186, and one or more peripheral device. The network 186 may interface with the processor 170 in a variety of ways, such as by optical and/or electronic interfaces, and may use a plurality of network topographies and protocols, such as Ethernet, TCP/IP, circuit switched paths, file transfer protocol, packet switched wide area networks, and combinations thereof. For example, the one or more network 186 may be implemented as the Internet, a LAN, a wide area network (WAN), a metropolitan network, a wireless network, a cellular network, a GSM-network, a CDMA network, a 3G network, a 4G network, a satellite network, a radio network, an optical network, a cable network, a public switched telephone network, an Ethernet network, and combinations thereof. The network 186 may use a variety of network protocols to permit bi-directional interface and communication of data and/or information between the processor 170, the network 186, and the one or more peripheral device. The communications between the processor 170 and the one or more peripheral device, facilitated by the network 186, may be indicative of communications between the processor 170, the one or more reader 150, and the one or more periphery device.

In one embodiment, the processor 170, the non-transitory computer readable medium 172, the input device 178, the output device 180, and the communications device 188 may be implemented together as a smartphone, a PDA, a tablet device, such as an iPad, a netbook, a laptop computer, a desktop computer, or any other computing device configured to interface with the analyte testing device 140.

The non-transitory computer readable medium 172 may store the processor executable code 174, which may comprise a testing and calibration program 174-1. The non-transitory computer readable medium 172 may also store other processor executable instructions 174-2 such as an operating system and application programs such as a word processor or spreadsheet program, for example. The other processor executable instructions 174-2, in one embodiment, may also contain processor executable instructions configured to tally testing and calibration processes performed by the testing and calibration program 174-1 in relation to a number of sample testing devices 14 stored on the analyte testing material web 10 to allow automated inventory tracking and ordering of additional analyte testing material webs 10 or analyte testing devices 90 or 120, or notify a user of low inventory and prompt re-order. The processor executable instructions for the testing and calibration program 174-1 and the other processor executable instructions 174-2 may be written in any suitable programming language, such as C++, C#, or Java, for example.

Figure 11:
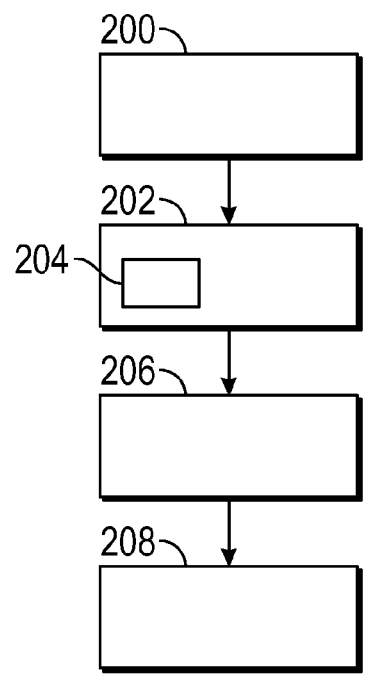
FIG. 11 shows a block diagram of a calibration program in accordance with the present disclosure.

Referring now to FIG. 11, therein shown is a diagrammatic representation of one embodiment of the testing and calibration program 174-1. As shown in FIG. 11, in one embodiment, the testing and calibration program 174-1, when executed, may calibrate the one or more reader 150 by causing the processor 170 to advance one of the plurality of sample testing devices 14 of the analyte testing material 10 to the read position 162, as indicated by block 200. The read position 162 may be a position at which one of the sample testing devices 14 is aligned with or otherwise may be read by the one or more reader 150, as described in more detail above. The calibration program 174-1 may then cause the processor 170 to introduce a control fluid to the sample testing device 14 at the read position 162, as indicated by block 202. The control fluid may enable calibration of the one or more reader 150 by creating a known calibration signals 204 when exposed to one of the sample testing devices 14 and read by the one or more reader 150. The processor 170 may receive the calibration signal 204 from the one or more reader 150 indicative of the one or more reader 150 reading an interaction between the control fluid and one or more testing element 32 of the analyte testing material web 10, as indicated at block 206. The processor 170 may then calibrate the one or more reader 150 to reconcile any difference between the calibration signal 204 and an expected calibration signal for the control fluid, as indicated by block 208.

Figure 12:
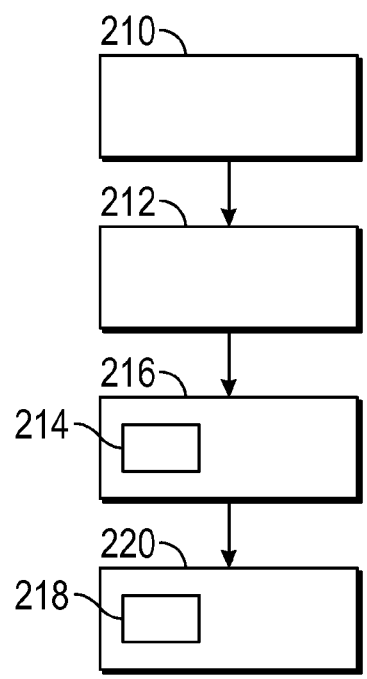
FIG. 12 shows a block diagram of a testing program in accordance with the present disclosure.

Referring now to FIG. 12, in one embodiment, the testing and calibration program 174-1 may test a sample for an analyte of interest by causing the processor to advance one of the sample testing devices 14 of the analyte testing material web 10 to the read position 162, as indicated by block 210. The testing and calibration program 174-1 may cause the processor 170 to introduce one or more sample to the sample testing device 14 in the read position 162, as indicated by block 212. The processor 170 may receive one or more testing signals 214 from the one or more reader 150 indicative of testing of the one or more sample for the analyte of interest, as indicated at block 216. The processor 170 may then output results 218 indicative of the one or more testing signals 214, as indicated by block 220. The processor may output the results 218 via a user interface coupled to the controller 152 and configured to output user readable signals indicative of the testing signals 214 received by the processor 170 of the controller.

While the present disclosure has been described in connection with the exemplary embodiments of the various FIGS., it is not limited thereto and it is to be understood that other similar embodiments may be used or modifications and additions may be made to the described embodiments for performing the same function of the present disclosure without deviating therefrom. Therefore, the present disclosure should not be limited to any single embodiment, but rather should be construed in breadth and scope in accordance with the appended claims. Also, the appended claims should be construed to include other variants and embodiments of the present disclosure, which may be made by those skilled in the art without departing from the true spirit and scope of the present disclosure.

What is claimed is:

1. An analyte testing material web, comprising:
   a material web having a first surface, a second surface opposite the first surface, a first side, and a second side; and
   a plurality of distinct sample testing devices positioned on the first surface of the material web, each of the plurality of sample testing devices having an inlet, an outlet, a fluid channel, and one or more testing elements within the fluid channel and configured to analyze one or more analyte within a sample applied to the inlet of one of the plurality of sample testing devices
   wherein the material web is a first material web having a first surface, a second surface opposite the first surface, and a thickness extending between the first and second surfaces, and each of the plurality of distinct sample testing devices comprising:
   the one or more testing elements connected to the first surface of the first material web;
   a second material web having a first surface, a second surface opposite the first surface, a thickness extending between the first and second surfaces, and a plurality of openings, the second surface of the second material web overlapping the first surface of the first material web such that the plurality of openings form a plurality of wells defined by the thickness of the second material web and the first surface of the first material web, each of the plurality of wells defining the fluid channel of one of the sample testing devices encompassing at least one of the one or more testing elements;
   a third material web having a first surface, a second surface opposite the first surface, a thickness extending between the first and second surfaces, a plurality of inlets, and a plurality of outlets, the second surface of the third material web overlapping the first surface of the second material web such that certain of the plurality of inlets and certain of the plurality of outlets enable fluid communication with each of the plurality of wells, wherein each of the plurality of inlets form the inlet of one of the sample testing devices and each of the plurality of outlets form the outlet of one of the sample testing devices; and
   one or more testing elements positioned on the second surface of the third material web such that the at least one of the one or more testing elements of the third material web are encompassed along with the one or more testing elements of the first material web within the fluid channel of one of the sample testing devices.

2. The analyte testing material web of claim 1, wherein the material web has perforations substantially adjacent to the first side and the second side, the perforations configured to enable advancement of the material web via one or more sprocket-wheels.

3. The analyte testing material web of claim 1, wherein the one or more testing elements are electrochemical sensors and each of the plurality of sample testing devices has a contact electrically connected thereto.

4. The analyte testing material web of claim 3, wherein the contacts and the one or more testing elements are positioned on the first surface of the material web and the material web further comprising a dielectric material web having a first surface, a second surface opposite the first surface, a thickness extending between the first and second surfaces, and a plurality of openings, the dielectric material web positioned to cover and thereby isolate the contacts and positioned such that certain of the plurality of openings of the dielectric material web are adjacent to the inlets and outlets of certain of the plurality of sample testing devices.

5. The analyte testing material web of claim 3, wherein the contacts are positioned on the second surface of the material web opposite the plurality of sample testing devices and connected to the one or more testing elements by vias extending between the first and second surfaces of the material web.

6. The analyte testing material web of claim 1, wherein the one or more testing elements are formed from one or more dry reagent material.

7. A method of making an analyte testing material web, comprising:
applying a plurality of testing elements to a first surface of a first material web, the first material web having the first surface, a second surface opposite the first surface, and a thickness extending between the first and second surfaces;
applying a second material web to the first surface of the first material web, the second material web having a first surface, a second surface opposite the first surface, a thickness extending between the first and second surfaces, and a plurality of openings forming a plurality of wells defined by the thickness of the second material web and the first surface of the first material web, each of the plurality of wells defining a fluid channel encompassing at least one of the plurality of testing elements;
applying a third material web to the first surface of the second material web, the third material web having a first surface, a second surface opposite the first surface, a thickness extending between the first and second surfaces, a plurality of inlets, and a plurality of outlets, the third material web being applied to the second material web such that certain of the plurality of inlets and certain of the plurality of outlets enable fluid communication with each of the plurality of wells; and
applying a plurality of testing elements to the second surface of the third material web such that the at least one of the plurality of testing elements of the third material web are encompassed along with at least one of the plurality of testing elements of the first material web within the fluid channel of one of the sample testing devices.

8. The method of claim 7, further comprising perforating at least one of the first, second, and third material webs substantially adjacent to a first side and a second side thereof, and wherein the perforations formed by perforating the at least one of the first, second, and third material webs enable advancement of the first, second, and third material webs via one or more sprocket-wheels.

9. The method of claim 7, wherein the one or more testing elements are positioned on the first material web by a method from a group consisting of: screen printing, stencil, ink jetting, aerosol, jetting, electrodeposition, and rotogravure.

10. The method of claim 7, wherein the plurality of sample testing devices are positioned on the first material web and spaced a distance apart from one another along the first material web.

11. The method of claim 7, wherein the one or more testing elements are a plurality of testing elements and certain of the plurality of testing elements are positioned on the first material web grouped together to form a plurality of testing groups, the testing groups being spaced a distance apart from one another along the first material web.

12. The method of claim 7, wherein the one or more testing elements are electrochemical sensors and each of the one or more testing elements has a contact electrically connected thereto.

13. The method of claim 12, wherein the contacts and the one or more testing elements are positioned on the first surface of the first material web and the method further comprising applying a dielectric material web between the first surface of the first material web and the second surface of the second material web to cover and thereby isolate the contacts and positioned such that a plurality of openings of the dielectric material web are adjacent to the plurality of openings of the second web to form wells defined by the thickness of the second material web, a thickness of the dielectric material web, and the first surface of the material web.

14. An analyte testing device, comprising:
a housing having at least one opening;
a reel positioned within and supported by the housing; and
an analyte testing material web connected to the reel and wound about the reel, the analyte testing material web having a material web and a plurality of distinct sample testing devices positioned on the material web, the material web has a first surface, a second surface opposite the first surface, a first side, and a second side opposite the first side, and each of the plurality of sample testing devices having an inlet, an outlet, a fluid channel, and one or more testing elements configured to analyze one or more sample applied to one or more of the plurality of distinct sample testing devices;
wherein the material web is a first material web having a first surface, a second surface opposite the first surface, and a thickness extending between the first and second surfaces, and each of the plurality of distinct sample testing devices comprising:
the one or more testing elements connected to the first of the first material web;
a portion of a second web having a first surface, a second surface opposite the first surface, a thickness extending between the first and second surfaces, and an opening, the second surface of the second material web overlapping the first surface of the first material web such that the opening forms a well defined by the thickness of the second material web and the first surface of the first material web, the well defining the fluid channel of one of the sample testing devices encompassing at least one of the one or more testing elements; and
a portion of a third material web having a first surface, a second surface opposite the first surface, a thickness extending between the first and second surfaces, an inlet, and an outlet, the second surface of the third material overlapping the first surface of the second material web such that the inlet and the outlet enable fluid communication with the well.

15. The analyte testing device of claim 14, wherein the material web has perforations substantially adjacent to the first side and the second side, the perforations configured to enable advancement of the material web via the reel, wherein the reel is provided with an opening surrounded by a plurality of ridges.

16. The analyte testing device of claim 14, wherein the reel is a first reel positioned within the housing and a second reel is positioned within the housing, and wherein the analyte testing material web is connected to the first and second reels such that the analyte testing material web is wound about and transferrable between the first and second reels.

17. The analyte testing device of claim 14, wherein the plurality of distinct sample testing devices are positioned on the material web spaced a distance apart from one another along the material web.

18. The analyte testing device of claim 14, wherein certain of the one or more testing elements are positioned on the material web grouped together to form a plurality of testing groups, the testing groups being spaced a distance apart from one another along the material web.

19. The analyte testing device of claim 18, wherein the one or more testing elements are electrochemical sensors and each of the one or more testing elements has a contact electrically connected thereto and wherein the contacts are positioned on the second surface of the material web opposite the one or more of testing elements and connected to the one or more of testing elements by vias extending between the first and second surfaces of the material web.

20. The analyte testing device of claim 14, wherein the one or more of the testing elements are formed from one or more dry reagent material.

\* \* \* \* \*